United States Patent [19]

Novello

[11] 4,282,878

[45] Aug. 11, 1981

[54] ELECTRODE STRUCTURE FOR ELECTROCARDIOGRAPH AND RELATED PHYSIOLOGICAL MEASUREMENTS AND THE LIKE

[75] Inventor: Peter P. Novello, North Andover, Mass.

[73] Assignee: Vaughn Corporation, Salisbury, Mass.

[21] Appl. No.: 67,342

[22] Filed: Aug. 17, 1979

[51] Int. Cl.³ .............................................. A61B 5/04
[52] U.S. Cl. .................................................. 128/641
[58] Field of Search ............................. 128/639–641, 128/643, 644, 783, 798, 802, 803

[56] References Cited

U.S. PATENT DOCUMENTS

| | | | |
|---|---|---|---|
| 1,583,087 | 5/1926 | Morse | 128/798 |
| 3,085,577 | 4/1963 | Berman et al. | 128/641 |
| 3,498,291 | 3/1970 | Bunn | 128/644 |
| 4,040,412 | 8/1977 | Sato | 128/640 |
| 4,161,174 | 7/1979 | Mercuri | 128/641 |
| 4,166,456 | 9/1979 | Wilson | 128/640 |

*Primary Examiner*—Lee S. Cohen
*Attorney, Agent, or Firm*—Rines and Rines, Shapiro and Shapiro

[57] ABSTRACT

This disclosure is concerned with a two-piece, similar metal-plated plastic mating stud and eyelet electrode structure for electrocardiograph or similar physiological or bioelectric measurements, embodying internal resilient ring and groove sealing members for preventing corrosive electrolytic gel interactions with the interfaces of the electrode assembly that can otherwise produce erratic electrical performance.

6 Claims, 3 Drawing Figures

ELECTRODE STRUCTURE FOR ELECTROCARDIOGRAPH AND RELATED PHYSIOLOGICAL MEASUREMENTS AND THE LIKE

The present invention relates to electrode structures for electrocardiograph and related physiological measurements and the like, being more particularly though not exclusively directed to patient-applied electrodes pre-gelled with electrolytic pastes, gels or the like to provide good electrical conduction between the electrode and the skin of the patient.

For many years the problems of electrode construction, attachment and use with human patients and animals for electrocardiograph (ECG) and Apnea monitoring and related physiological testing and measurements have been systematically approached with steady improvement in apparatus and in cost-reduction that permit of simple application and disposable advantages. Prior constructions are exemplified, for example, by U.S. Pat. Nos. 3,085,577; 3,170,459; 3,487,827; 3,464,404; 3,515,619; 3,518,984; 3,581,736; 3,590,810; 3,599,629; 3,602,216; 3,692,216; 3,696,807; 3,701,346; 3,731,435; 3,752,151; 3,805,769; 3,820,531; 3,828,766; 3,865,099; 3,882,853; 3,901,218; 3,945,384; 3,946,730; 4,027,664; 4,029,086; and 4,067,322. Particularly in the more recent of the above, disposable pre-gelled ECG electrodes and the like are described, the earlier commercial versions of which involved two-piece electrode constructions having a silver-plated brass stud swaged onto a silver-plated brass eyelet through an adhesive-coated film or foam, and with a gel pad placed in contact with the eyelet and packaged into a foil pouch. Among the problems with this type of assembly was corrosion of the eyelet (actually through the silver plating and with the brass) and sporadic leaks of gel to the stud. This corrosion activity also led to erratic electrical offset voltages and drift in the same, the significance of which will now be explained.

As explained, for example, in *Biophysical Measurements* Chapter 16, "Electrodes", pp. 219-232, Peter Strong, 1970, Tektronics Inc., the above-described type of electrode assemblies generates an "offset potential" which is defined as the difference between the half cell D.C. potentials produced across the metal-electrolyte interfaces of the two metals comprising the electrode. When these electrodes are connected to a subject to record bioelectric phenomena such as electrocardiograph (ECG) signals upon a DC-coupled recorder (such as chart recorder or an oscilloscope monitor), longer-term offset potentials appear as baseline "drift", and shorter-term variations as "noise" on the recorded trace that otherwise demonstrates A.C. signal pulses (of frequency range of about 0.05 to 100 Hertz for ECG signals). Mechanical disturbance of an electrode half-cell junction (i.e. gel to metal interface) may create an extensive drifting or wandering of the baseline. When it is reflected that AAMI proposed standards (Association of the Advancement of Medical Instrumentation) specify that ECG monitors should have an offset tolerance of 200 mv, such that when electrodes exhibiting such an offset potential are connected to a patient who is connected to an ECG machine, the ECG waveform (signals of the order of 1.5 mV) should still be visible on the monitor, large or unstable offset drifts make it difficult to interpret the recorded or monitored trace. With some monitors, for example, a drift of over, say 30 $\mu$V/sec. may result in sufficient baseline movement as to render interpretation of the ECG signal difficult or even impossible.

Resort has been had to mitigating against the above-described artifacts by choosing electrode materials that reduce the magnitude of the offset potential and by taking steps, as with electrode attachment techniques, to reduce the chance for disturbing the electrode surfaces. The use of a silver chloride sensing element and a relatively rigid housing and confined electrolytic fluid package have been found to help to some degree as described, for example, in the bulletin "DISPOS-EL patient monitoring system", B-D Electrodyne, and in the bulletin of Andover Medical Incorporated, the assignee of the present invention, "AMI Electrode/Cabling Systems" 1978.

Plaguing the art, however, has also been the difficulty in preventing the electrolytic gel from leaking to the electrode studs, causing corrosion and serious offset potential drift, with resultant poor electrical performance. While the adoption of chlorided solid silver eyelets resulted in better electrical results and lower offsets, this improvement was obtained only so long as leaking was prevented. As the cost of silver was rising, however, manufacturers replaced the chlorided solid silver eyelet with a chlorided silver-plated plastic eyelet. But a good seal has not heretofore always been possible with manufacturing and material condition variations and lack of consistent reliability thereof, such that there often exists a leak syndrome which, up to the present invention, has not been satisfactorily remedied. The variations in offset potential caused by such leaking with chlorided silver-plated plastic parts still present serious difficulties.

It is to the solution of such problems in the use of chlorided silver-plated plastic electrode parts and the like that the present invention, from one of its principal aspects, is directed; it being an object of the invention to provide a new and improved electrode assembly of the character described that largely obviates the leakage and offset potential change problems above discussed.

An additional object of the invention is to provide an improved, inexpensive, disposable electrode structure, particularly though not necessarily exclusively adapted for ECG and related physiological and bioelectric measurements and the like, of more general utility, as well.

Other and further objects are explained hereinafter and are more particularly pointed out in the appended claims. In summary, however, from one of its important aspects, the invention embraces an electrode structure for electrocardiograph and related physiological measurements and the like having, in combination, cooperative thin plastic stud and eyelet members each plated with the same highly conductive surface and having corresponding flange surfaces that abut when the members are mated; cooperative sealing ring and groove means integrally provided in the plastic at intermediate regions of the abutting flange surfaces of the stud and eyelet members to provide resilient positive swaged lock-sealing therebetween; and means for mounting electrolytic gel means with the members, with the sealing ring and groove means preventing leakage of the gel means into the interface between the members. Preferred or best mode constructional details are hereinafter set forth.

The invention will now be described with reference to the accompanying drawing,

FIG. 1 of which is a longitudinal cross-sectional view of the two-piece construction of the electrode of the invention in preferred form and in expanded position before the parts are assembled;

Figure 1:
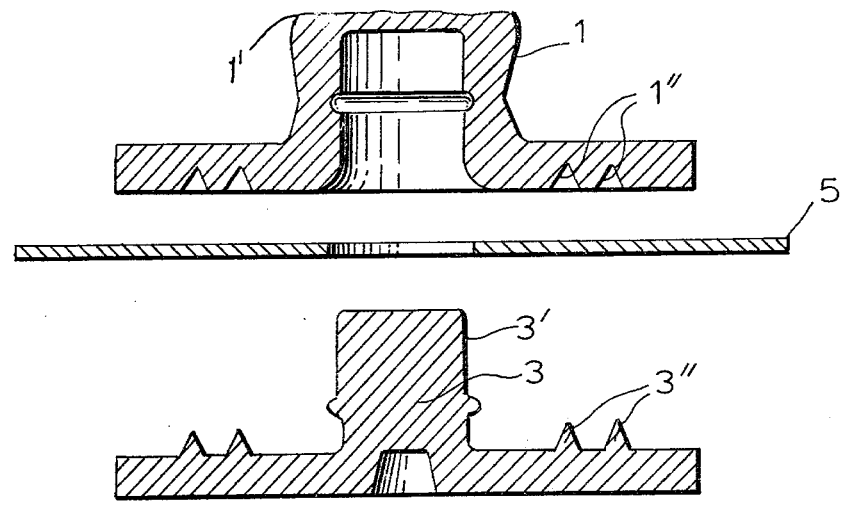

Referring to FIG. 1, the novel electrode construction of the invention is shown comprising matable stud and eyelet electrode pieces 1 and 3, respectively, with an interposable sheet 5 for carrying any desired type of depending electrolyte gel or similar pocket, such as that later described in connection with the embodiments of FIG. 3. The stud 1 and eyelet 3 are preferably made of thin plastic material, such as high density styrene or acrylonitrile butadiene styrene or the like, and are externally plated with a highly conductive metal such as silver, to provide the respective same-metal electrode surfaces 1' and 3'. If desired, these surfaces may be chlorided. The stud 1 is preferably dimpled as shown to enable snap-type electrical connection to leads; and the eyelet 3 is provided with an external annular ring for snap-engagement with a corresponding recess in the inner wall of the stud 1. In accordance with the invention, furthermore, the lateral upper flange surface of the eyelet 3 is provided with a pair of upwardly protuding, intermediately disposed, concentric rings 3" for mating with a corresponding pair of concentric circular grooves 1" in the under flange surface of the stud 1.

Figure 2:
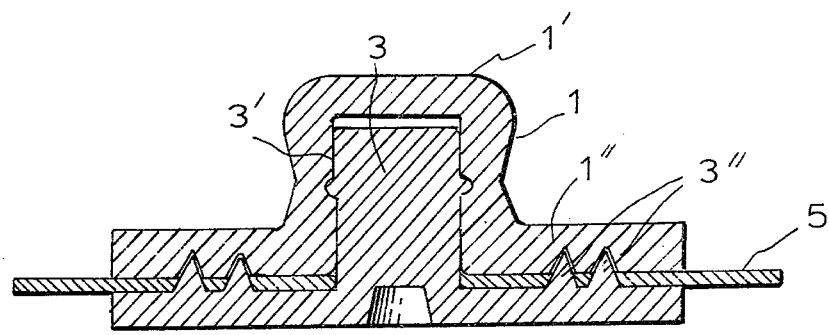
FIG. 2 is a view similar to FIG. 1, but with the electrode parts assembled.

When the eyelet 3 is swaged into locked abutting engagement with the stud 1, FIG. 2, with the centrally apertured thin sheet 5 interposed, the rings 3" will resiliently snap-seal squeezing sheet 5 within the grooves 1", creating a leak-proof positive seal that prevents any gel from entering the interface between the two electrode pieces 1 and 3. As later more fully described, this has completely obviated the before-discussed dissimilar-metal and gel leakage-corrosion problems that have resulted in erratic electrical performance, including relatively large off-set potentials and drifting thereof.

As previously stated, the use of the plated plastic construction maintains the advantage of lower cost than solid silver components, and eliminates electrical problems associated with gel leakage with prior two-piece electrode constructions. The ability to plate both the stud and eyelet with the same metal, furthermore, also prevents bi-metallic potentials of present-day electrode assemblies.

Figure 3:
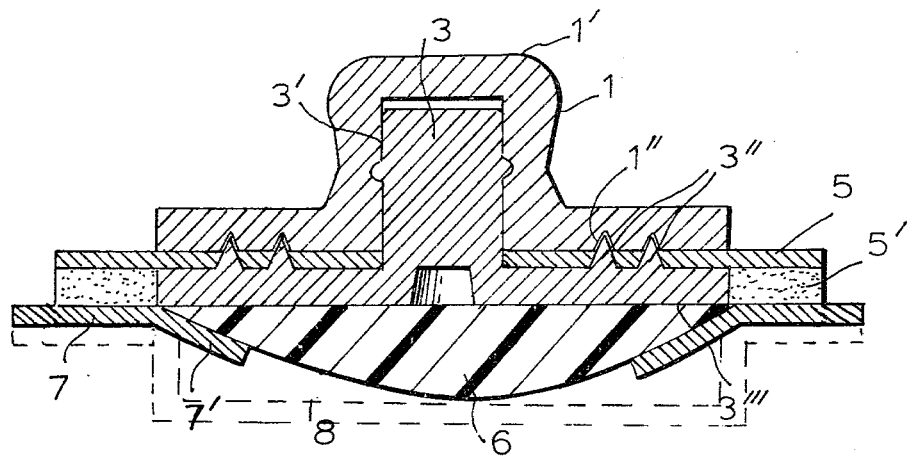
FIG. 3 is a similar view of an illustrative complete electrode assembly using the structure of FIGS. 1 and 2.

In FIG. 3, the carrier sheet 5 is shown holding a gel pocket of the type described in copending U.S. patent application Ser. No. 760,099, of the assignee of the present invention, filed Jan. 17, 1977 by Ronald Wilson, now U.S. Pat. No. 4,166,456 issued Sept. 4, 1979. In this construction, a base sheet 7 of flexible, stretchable and preferably porous light-transmitting material (to permit skin breathing and observation) is secured or mounted to the carrier sheet 5 by an adhesive layer 5' carried by the lower surface exposed peripheral portions of the sheet 5. The base sheet 7 is provided with an open pocket 8 containing an electrolytic gel pad 6 (impregnated with salt and agar, for example) the lower portion only of which is exposed at the opening 8 for contact with the skin. The lower surface of the sheet 7 is provided with an adhesive coating 7' to enable attachment to the skin (and, prior to use, to a protective base cup, shown dotted, that seals the gel pocket for storage). By extending the open pocket of the sheet 7 partly down the gel pad 6, and shaping the gel pad in oval or lenticular shape, the central part only of the gel pad will protude outside the opening of the pocket so that the structure can conformably shape and cushion to the skin, presenting a desirable low profile.

In view of the sealed two-piece construction of the invention, as before explained, the gel cannot enter the interface between the electrode pieces, obviating the large offset potential and drift problems of prior art constructions. The following table compares the significant improvement in these particulars attainable with the invention, as distinguished from typical prior art two-piece electrode constructions before discussed:

| Electrode Construction | Offset Potential Problem Units | Drift (Average) Problem Units |
| --- | --- | --- |
| Silver plated brass stud | 85 mV | 41.6 μV/sec. |
| Solid Silver chlorided eyelet | (best units-4.1 mV) | (best units-1.4 μV/sec.) |
| Silver-plated brass stud-Solid silver eyelet | 55 mV | 41. μV/sec. |
| Chloride silver-plated plastic stud and eyelet of present invention | (no problem) 1.7 mV | (no problem) 1.08 μV/sec. |

In preferred construction, that plating of the plastic eyelet and stud may be of from 100 to 500 microinches; the flange wall thickness of the order of 0.76 mm; the seal rings of the order of 0.25 mm. in height; and the seal rings located at positions one-third and two thirds of the distance inward of the flange to provide optimal sealing.

While the invention has been shown in the embodiment of FIG. 3 as applied to a particular type of depending gel pocket, clearly other constructions may also be used with the two-piece snap electrode assembly of the invention. Though, in preferred form, the sealing rings are shown on the eyelet flange and the cooperative grooves on the stud flange, these positions could be reversed. Whereas the coating on the stud and eyelet has been described as of the same noble metal, such as silver, either or both of these members may also have the surface of the silver chlorided, which is of particular advantage for improved electrical performance with the depending gel. Further modifications will also suggest themselves to those skilled in the art, without departing from the spirit and scope of the invention, as defined in the appended claims.

What is claimed is:

1. An electrode structure for electrocardiograph and related physiological measurements and the like having, in combination, cooperative thin plastic stud and eyelet members, each plated with the same highly conductive surface, said members having a mated interface and cooperative flange surfaces extending from said interface, means for securing an electrolytic gel to the conductive surface of the eyelet and means for inhibiting leakage of the gel into said interface between the members, said leakage inhibiting means including cooperative sealing ring and groove means in the respective flange surfaces of said members for providing positive swaged lock-sealing therebetween.

2. An electrode structure as claimed in claim 1 and in which the said same highly conductive surface is silver and is chloride coated upon at least the eyelet member.

3. An electrode structure as claimed in claim 1 and in which said sealing ring and groove means comprise a pair of cooperative concentric rings and grooves.

4. An electrode structure as claimed in claim 1 and in which said securing means includes a thin centrally apertured carrier sheet interposed between the mated eyelet and stud.

5. An electrode structure as claimed in claim 4 and in which a stretchable sheet is adhesively secured to an under periphery of said carrier sheet and is provided with a depending open pocket containing said gel, the stretchable sheet having a lower surface provided with adhesive extending to the opening of said pocket.

6. An electrode structure as claimed in claim 5 and in which the said gel is substantially lenticular in shape and the opening of the pocket exposes only the central part of the gel which protrudes through said opening to permit a cushion-like shaping to the skin of a user, with the adhesive securing to the skin about the pocket and enabling a low profile attachment thereto.

* * * * *